United States Patent [19]

Smith et al.

[11] Patent Number: 4,852,577

[45] Date of Patent: Aug. 1, 1989

[54] HIGH SPEED ADAPTIVE ULTRASONIC PHASED ARRAY IMAGING SYSTEM

[75] Inventors: Stephen W. Smith, Rockville, Md.; Gregg E. Trahey, Hillsborough, N.C.

[73] Assignee: The United States of America as represented by the Department of Health and Human Services, Washington, D.C.

[21] Appl. No.: 178,736

[22] Filed: Apr. 7, 1988

[51] Int. Cl.[4] ..................... A61B 8/00

[52] U.S. Cl. ..................... 128/660.07; 73/625

[58] Field of Search ..................... 128/660.07; 73/625

[56] References Cited

U.S. PATENT DOCUMENTS

| | | | |
|---|---|---|---|
| 4,140,022 | 2/1979 | Maslak . | |
| 4,149,420 | 4/1979 | Hutchison et al. . | |
| 4,279,157 | 7/1981 | Schomberg et al. . | |
| 4,566,459 | 1/1986 | Umemura et al. . | |
| 4,633,883 | 1/1987 | Matsui | 128/660.07 |
| 4,700,573 | 10/1987 | Savord | 73/625 |

OTHER PUBLICATIONS

Phillips, D. J., Smith, S. W., von Ramm, O. T., and Thurstone, F. L. "Sampled aperture techniques applied to B-mode echoencephalography", Acoustical Holography, vol. 6, N. Booth, ed., 103-120, Plenum Press (New York and London, 1975).

Jellins J. and Kossoff G., "Velocity Compensation in Water-Coupled Breast Echography," Ultrasonic 11, 223-226, 1973.

Smith, S. W., Phillips D. J., von Ramm O. T. and Thurstone F. L., "Some Advances in Acoustic Imaging Through Skill," Ultrasound tissue characterization II, M. Linzer, ed., NBs Pub. #525, Jun. 1978, 209-218.

Miller-Jones S. M., "Automated Arrival Time Correction for Ultrasonic Cephalic Imaging." Ph.D. Thesis, Duke University, Durham, N.C., 1980.

Hirama M., Ikeda O. and Sato T. "Adaptive Ultrasonic Array Imaging System Through an Inhomogeneous Layer," *J. Acoust. Soc. of Amer.* 71(1), 100-109, 1982.

Hirama M. and Sato t. "Imaging Through an Inhomogeneous Layer by Least-mean-square Error Fitting," *J. Acoust. Soc. Amer.* 75(4), 1142-1147, Apr., 1984.

Muller R. A. and Buffington A., "Real Time Correction of Atmospherically Degraded Telescope Images Through Image Sharpening," *J. Opt. Soc. Amer.* 64(9), 1200-1210, 1974.

Attia E. H., "Phase Synchronizing Large Antenna Arrays Using the Spatial Correlation Properties of Radar Clutter," Ph.D., Dissertation, University of Pennsylvania, 1984.

Steinberg B. D. and Subbaram H. M., "Self Calibration of Phased Array Using the Muller Buffington Theorem and Transmitter Location Diversity" Valley Forge Research Center Quarterly Report #50, 31-45, 1986.

Steinberg B. D., "Distortion Correction by Image Feedback Control" Valley Forge Research Center Quarterly Report #49, 54-58, 1986.

*Primary Examiner*—Francis Jaworski

*Attorney, Agent, or Firm*—Browdy & Neimark

[57] ABSTRACT

An ultrasonic phased array imaging system is provided which includes a normal mode and an adaptive mode of operation. The adaptive mode adjusts the delay associated with each element in the transducer such that the average image brightness of the region of interest is maximized. A motion detector is provided for determining when the transducer has been moved a distance sufficient to render the previous adaptive measurements possibly invalid whereupon the system automatically reenters the normal mode. A method of operating the ultrasonic phased array imaging system is also provided.

20 Claims, 8 Drawing Sheets

| | |
|---|---|
| 0 | SCAN DATA SET #1, LINE #1 SINE WORD/COSINE WORD |
| 1 | TRANSMIT DATA, 64 BITS |
| 2 | RECEIVE DATA, FOCAL ZONE #1, 64 BITS |
| | |
| 7 | FOCAL ZONE #6, 64 BITS |
| 8 | LINE #2 SINE WORD/COSINE WORD |
| | |
| 1023 | LINE #128 RECEIVE DATA, FOCAL ZONE #6 |
| 1024 | SCAN DATA SET #2, LINE #1 SINE WORD/COSINE WORD |
| 1025 | TRANSMIT DATA |
| | |
| 2047 | LINE #128 RECEIVE DATA, FOCAL ZONE #6 |

TO FIG.7B

HIGH SPEED ADAPTIVE ULTRASONIC PHASED ARRAY IMAGING SYSTEM

This application is related to U.S. patent application Ser. No. 016,427 filed Feb. 19, 1987 in the name of Smith et al, the entire disclosure of which is hereby incorporated by reference.

BACKGROUND OF THE INVENTION

1. Field of the Invention

The present invention relates to improvements in ultrasonic imaging; and, more particularly, to a high speed adaptive ultrasonic phased array imaging system. The system employs an image sharpening process which maximizes the average brightness of image texture within a selected region of interest by varying the phased array scan data of array elements for the image lines within the region.

2. The Prior Art

Ultrasonic imaging has been extensively applied in virtually every medical specialty in the form of pulse echo B-mode tomography (See Wells, 1977). This modality displays echoes returning to the transducer as brightness levels proportional to echo amplitude. The transducer is mechanically or electronically translated or steered in one dimension. The brightness levels are displayed versus echo range and transducer position or orientation, resulting in cross sectional images of the object in the plane perpendicular to the transducer face.

Ultrasound B-scan systems may incorporate piston-like piezoelectric transducers fabricated to produce a fixed focus achieving diffraction limited spatial resolution in the lateral direction. These are mechanically scanned to obtain the tomographic image. Alternatively, segmented array transducers are now used in many medical ultrasound imaging devices (See Wells, 1977). A number of types of transducers may be used. In one type of transducer, an annular phased array of transducer elements are arranged in a bulls-eye pattern (See Melton et al, 1978) and incorporated into a mechanically driven imaging system. Annular arrays enable focusing of the ultrasound beam during both transmit and receive operations, including receive mode dynamic focusing over a long depth of focus, by properly timing or "phasing" the transmit pulses and selectively delaying the receive mode echoes.

Another type of transducer, a sequential linear phased array (see Wells, 1977), operates by sequentially activating groups of piezoelectric elements for the transmit-receive process in the on-axis direction. Each group of elements produces a single image line resulting in a rectangular image format. As with the annular array, transmit focusing and receive mode dynamic focusing are achieved by proper timing of the transmit signals and delaying receive mode echoes. A third type of transducer, a sectored linear phased array consists of a single group of transducer elements which is not only focused by also steered over a sector angle in transmit and receive (Tx and Rx) by properly timing the transmit signals and receive mode echoes (see von Ramm et al, 1983).

In each type of phased array imaging system, the correct timing relations for transmit and/or receive modes are pre-calculated and incorporated into the imaging device as hard wired circuitry or data contained in the software memory of a digitally controlled system. In phased array imaging systems in the prior art, this timing or phasing data is determined by assuming propagation of ultrasound pulses through a homogeneous tissue medium with a uniform velocity of sound, usually 1540 m/sec. The assumption of a constant velocity of sound in the body is also the design basis in all ultrasound scanning systems for converting round trip pulse-echo time of flight into target range in the image.

Unfortunately, this simplest model of all human tissues is not valid. The body is actually composed of inhomogeneous layers of differing tissues (fat, muscle and bone) with bumps and ridges of varying thicknesses and different acoustic velocities. These layers intervene between the transducer and the internal organ of interest. The propagation velocity of ultrasound varies from approximately 1470 m/sec in fat to greater than 1600 m/sec in muscle and nervous tissue to as much as 3700 m/sec in bone (see Goss et al). If an incorrect average velocity is chosen, B-scan imaging is known to result in an image range error and compound scan registration errors for all ultrasound systems. A method to minimize these errors by offering a selectable average velocity has been previously described by Jellins and Kossoff (1973) for a water coupled ultrasound breast scanner.

Under the assumption of a uniform tissue medium of constant velocity, the presence of inhomogeneous tissues can also result in image artifacts, range shifts, geometric distortions, broadening of the transducer beam pattern which degrades the ideal diffraction limited lateral resolution, and increased side lobes which reduce the signal to noise ratio in the image. These problems occur in all types of pulse echo ultrasound systems to some degree. A worst case situation occurs in adult cephalic imaging through the skull layer where the problems are so severe that ultrasound imaging through the intact adult skull has been almost totally abandoned. Undesirable refraction effects from fat/muscle interfaces have also been noted in several clinical studies of abdominal ultrasound (see Muller et al, 1984) as well as in studies which simulate conditions in ultrasound breast imaging (see Davros et al, 1985).

The adverse effects of inhomogeneous nonuniform tissue layers have been analyzed by several investigators primarily in terms of unknown phase aberrations associated with the inhomogeneities introduced across the transducer aperture. Attempts have been made to overcome these aberrations using various signal processing techniques.

The present inventors have modeled the inhomogeneous tissue layers of varying thickness as planar layers of an assumed uniform thickness (see U.S. patent application Ser. No. 016,427 filed Feb. 19, 1987, incorporated herein by reference; and Smith et al, 1986). The refraction effects of these layers are then corrected in the sectored phased array data resulting in some improvement to image quality. In the case of adult cephalic imaging, the inventors have also described an on-line multiplacative receive mode signal processing technique (see Smith et al, 1976; and Smith et al, 1975) which improves image quality for the limited case of an intervening tissue layer whose aberration function is symmetric about the transducer center.

In recent years, attempts have been made to measure the phase aberration profile in front of the transducer for the purpose of phase correction. The present inventors applied this technique to ultrasound imaging (see Smith et al, 1978) by measuring the aberration function in front of the transducer array using the arrival time at each array element of signals from a single independent point source or point reflector. The sector scan phased array delay data for steering and focusing in the entire image was then updated using this measurement of the aberration function.

A similar technique was proposed by Hirama et al (1982) using echoes from one or a few discrete resolved point scatterers in the focal plane of an ultrasound array. In this case, the aberration function is measured along a single image line by varying the relative phase delays between two array elements at a time so as to maximize a quality factor relative to signal strength for the strongest single target in the desired focal plane. The measurement of the aberration function was used to correct the phased array data of an ultrasound C-scan in which the image plane is parallel to the transducer face. Hirama and Sato (1984) later realized the inadequacy of assuming discrete resolved point scatterers in a complex object and proposed a new technique for structured targets in which the spatial frequency contribution of the target is removed from the aberration measurement by extensive measurements of object spatial frequencies followed by image reconstruction via inverse Fourier transform.

It should be noted that the phase aberration function across the transducer aperture can change as a function of position or steering angle. The aberration is constant only over a region of target angle and target range known as the iso-planatic patch (IPP) (see Fried, 1974). Thus correction of phase aberration over an entire image using a phase aberration measurement or an image sharpening technique based on a single target angle and focal range usually is not valid. The size of the iso-planatic patch is inversely related to the severity of the transducer phase aberration, transducer aperture size and frequency. It has been demonstrated that the IPP for conventional phased array adult cephalic imaging is approximately 10° (see Miller-Jones, 1980). It is anticipated that the IPP for conventional abdominal scanning is larger.

Another technique to restore diffraction limited spatial resolution degraded by aberrations was proposed by Muller et al, 1974, for astronomical optical telescopes which all use spatially incoherent radiation. An image quality parameter such as the intensity to a power integrated over a region containing a star or bright spot is maximized by varying the positions of an array of mirrors comprising the telescope, thus restoring image resolution. Subsequent analysis of this image sharpening process for spatially coherent radiation such as radar, microwave imaging, and ultra-sound imaging was carried out by Steinberg et al (see Attia, 1984; Steinberg, 1986; and Steinberg et al, 1986). Their conclusion was that image sharpening using intensity quality factors was not valid for spatially coherent imaging except by using a single point target. They have proposed another technique to change a spatially coherent imaging device into a spatially incoherent system by means of transmitter location diversity (also known as "spatial compounding" in the medical ultrasound art). The spatial incoherence would then enable the use of the image sharpening technique of Muller and Buffington (see Muller et al, 1974) over complex objects to compensate for transducer phase aberrations.

The present inventors have discovered that these conclusions in the prior art are incorrect regarding compensation for phase aberration via image sharpening in spatially coherent medical ultrasound imaging devices. Since 1978, the understanding has developed (see Burckhardt, 1987; and Wagner et al, 1983) that the texture of medical ultrasound images of tissue consists primarily of a random speckle interference pattern resulting from the phasor summation of echoes from a large number of fine scatterers within the transducer resolution cell (see Burckhardt, 1987); and Wagner et al, 1983). The echoes from these particles exhibit phases uniformly distributed over 0 to 2 $\pi$ radians. Although the image brightness of an individual speckle is a random process, the means image brightness and variance over an area is predictable.

The inventors have recently demonstrated that individual speckle spots change unpredictably from bright points to null as the phase function or aberration changes across the transducer aperture. However, the inventors have also demonstrated that the average image brightness of speckle in a region of interest is predictably decreased by transducer phase aberrations. Thus, an individual speckle in the image cannot be used as an image sharpening target. However, the average brightness of many speckles over a region of interest can be used as a quality factor in an image sharpening process for a phased array ultrasound scanner. When the discrete specular targets are also present in a region of interest, image sharpening using mean brightness in that area is less effective. On the other hand, if the uniform image texture in the region contains significant contributions from ordered unresolved scatterers in tissue, the image sharpening technique still performs quite satisfactorily.

Applicants have recently become aware of yet another method in the art for phase aberration correction described by M. O'Donnell and S. Flax, although Applicants are unaware as of this writing of any publications or patents describing this method. In this method for a region of interest in an ultrasound speckle image, a cross correlation function is calculated between two channels N and N+1 of a phased array system. The phased array scan data between these two elements is varied until a maximum is achieved in the cross-correlation function. The process is then continued with element N+2 versus N+1. This method using a cross-correlation relies on a product, i.e., multiplication, rather than an integral or a sum, as in the instant invention.

The phase correction technique of the instant invention was achieved totally independently of the method of O'Donnell et al and is significantly different. The method of O'Donnell et al using a product operation (cross-correlation) is more sensitive to slight phase differences between channels N, N+1. As such it is more sensitive to noise than the instant invention in the environment of low signal to noise ratio of typical ultrasound imaging. The cross-correlation function is a much more complex operation than a simple integral and is therefore more time consuming, thus limiting its application to high speed systems. Furthermore, the method of O'Donnell et al must be performed on the radio-frequency echoes prior to envelope detection. These signals range from 3.5 to 20 MHz and thus require high speed analog-to-digital (A/D) conversion. The instant invention operates on the echo signal after envelope detection which reduces the frequency requirements to approximately 1 MHz and is much more naturally and easily adapted to conventional ultrasound scanners. Finally, the method of O'Donnell et al requires A/D conversion of every phased array channel whereas the instant invention requires A/D conversion of only the summed signal from all the phased array channels.

There is a final important concept. In 1983, it was demonstrated that the average size of the speckle interference pattern is predictable is measured by the statistical parameter, the normalized auto-convariance function or its Fourier Transform pair, the noise power spectrum (see Wagner et al, 1983). The average speckle size Sc in the lateral direction can be defined by the full width half maximum (FWHM) of the normalized auto-convariance function (ACVF). For a fully developed speckle with no transducer aberration, $$Sc \approx .8 \frac{\lambda Z}{D}$$

where λ is the transducer wavelength, Z is the transducer focal range, and D is the transducer aperture length. It has recently been discovered that the average speckle size is also affected by the transducer aberrations. The main lobe width of the speckle normalized auto-convariance function decreases in the presence of phase aberrations. Thus, the speckle size offers another independent parameter for adaptive processing to compensate for transducer phase aberrations.

In summary, the present inventors note the following differences between a number of the above-discussed techniques and the present invention.

Jellins and Kossoff (1973) describe a water coupled breast scanner which features a single selectable average velocity. They make no attempt to compensate for tissue layers of different velocities within the body to overcome phase aberration.

Smith et al (1987 & 1986) model inhomogeneous tissue layers of varying thickness and velocity as planar layers of varying velocity. They correct for refraction errors due to the planar layers (minor effect) but make no attempt to correct for other principal sources of phase aberration such as layers of varying thickness.

Smith et al (1976, 1975) described an on-line multiplicative receive model signal processing technique which would correct for an intervening tissue layer whose aberration function is symmetric about the transducer center. This is a rare occurrence and their scheme cannot correct for a generalized aberration.

Phillips et al (1975), Smith et al (1978) and Miller-Jones (1980) described a method to measure the aberration function of an intervening tissue layer using a point reflector in the body or a point source on the opposite side of the body from the transducer. Once the aberration function has been measured, the phased array scan data can be corrected to eliminate the effects of the aberrator. However such point targets are rare in the body so that this technique would seldom be useful. The use of a second external transducer which must be aligned with the phased array would be clumsy and complex and may not be practical.

Hirama et al (1982) described a similar technique using echoes from a single target or the strongest target of a group of discrete scatterers. But groups of discrete resolved targets seldom exist in the body so the technique is seldom practical.

Hirama et al (1984) later realized the inadequacy of assuming discrete resolved point scatterers in a complex object and proposed a new technique for structured targets in which the spatial frequency contribution of the target is removed from the aberration measurement by extensive measurements of the target spatial frequencies followed by image reconstruction via inverse Fourier transform.

A similar technique to restore diffraction limited spatial resolution degraded by aberration was proposed by Muller et al (1974) for astronomical optical telescopes which all use spatially incoherent radiation. An image quality parameter such as the intensity to any power is integrated over any sized region for discrete targets. This may include a single point target such as a single star or any arbitrary small region of an extended source such as planet or galaxy which has a bright spot. The critical difference between the instant invention and Muller et al (1974) is that for the spatially coherent radiation of medical ultrasound, an arbitrarily small region including only a few image points will not suffice. The texture of medical ultrasound images consist primarily of a random interference pattern called speckle which acts as multiplicative noise modulating the real objects in an ultrasound image. Thus individual image points or speckles in the image of an organ do not correspond to real objects within the organ. During a process of phase correction the brightness of individual speckles will oscillate, and the integral of intensity to any power over an arbitrary small region will also oscillate. The improvement of the instant invention over the prior art is that the inventors combined the knowledge of previous prior art schemes with the recent understanding of ultrasound speckle to arrive at the method which requires an integral over a statistically significant region of speckle to achieve an increase in integrated brightness as the phase correction proceeds to the solution.

A further difference between the instant invention and Muller et al is that for a uniform object such as a planet with no bright spot, the method of Muller et al will not converge. However, a uniform object in medical ultrasound produces the image speckle pattern described above. Thus the brightness integral over a sufficiently large region will serve as an adequate quality factor.

Attia (1984), Steinberg (1986) and Steinberg et al (1986) also realized the futility of applying the technique of Muller et al (1974) to spatially coherent radiation of medical ultrasound. Their solution, however, was to change ultrasound images into spatially incoherent images by the technique of transmitter location diversity (known as spatial compounding) in medical ultrasound. If ultrasound images approach spatial incoherence, the arbitrary size of the ROI of Muller et al (1974) may suffice.

The following is a list of articles cited above.

Attia E. H., "Phase synchronizing large antenna arrays using the spatial correlation properties of radar clutter," Ph.D. Dissertation, University of Pennsylvania, 1984.

Burckhardt C. B., "Speckle in ultrasound B-mode scans," IEEE *Trans. Son. Ultrason.*, 25(1) pp. 1–6, Jan. 1978.

Davros W. J., Madsen E. L. and Zagzebski J. A., "Breast mass detection by US: A phantom study", Radiology 156, 773–775, 1985.

Fried D. L., Isoplanatic aspects of predetection compensation imagery. Report #TR-131, Optical Science Consultants, Yorba Linda, Calif., 1974.

Goss S. A., Johnston R. L. and Dunn F., "Comprehensive compilation of empirical ultrasonic properties of mammalian tissues," *J. Acoust. Soc. Am.* 64(2), 423–457.

Hirama M. Ikeda O. and Sato T., "Adaptive ultrasonic array imaging system through an inhomogeneous layer," *J. Acoust. Soc. of Amer.* 71(1), 100–109, 1982.

Hirama M. and Sato T., "Imaging through an inhomogeneous layer by least-mean-sqaure error fitting," *J. Acoust. Soc. Amer.* 75(4), 1142–1147, April, 1984.

Jellins J. and Kossoff G., "Velocity compensation in water-coupled breast echography," *Ultrasonic* 11, 223–226, 1973.

Melton H. E., Jr. and Thurstone F. L. "Annular array design and logarithmic processing for ultrasonic imaging," *Ultrasonic in Medical and Biology* 4, 1–12, 1987.

Miller-Jones S. M., "Automated arrival time correction for ultrasonic cephalic imaging." Ph.D. Thesis, Duke University, Durham, N.C., 1980.

Muller N., Copperberg P. L., Rowley V. A., Mayo J., Ho B. and Li D.K.B., *Ultrasound Med.* 3, 515–519, 1984.

Muller R. A. and Buffington A., "Real time correction of atmospherically degraded telescope images through image sharpening," *J. Opt. Soc. Amer.* 64(9), 1200–1210, 1974.

Phillips, D. J., Smith, S. W., von Ramm, O. T., and Thurstone, F. L., "Sampled aperture techniques applied to B-mode echoencephalography", *Acoustical Holography, Vol.* 6, N. Booth, ed., 103–120, Plenum Press (New York and London, 1975).

Shattuk, D. P., Weinshenker M. D., Smith S. W. and von Ramm O. T., "Explososcan: a parallel processing technique for high speed ultrasound imaging with linear phased arrays," *J. Acoust. Soc. Amer.* 75(4), 1273–1282, 1984.

Smith S. W., Miller E. B., von Ramm O. T. and Thurston F. L., "Signal processing techniques to improve B-mode echoencephalography," *Ultrasound in Medicine,* D. N. White, Editor, Plenum Press, 1975, Vol. 1, 405–414.

Smith S. W., Phillips D. J., von Ramm O. T. and Thurstone F. L., "Real time B-mode echoencephalography," *Ultrasound in Medicine* 11, White & Barnes, Editors, Plenum Press, 1976, 373–382.

Smith S. W., Phillips D. J., von Ramm O. T. and Thurstone F. L., "Some advances in acoustic imaging through skill," *Ultrasonic tissue characterization II,* M. Linzer, ed., NBs Pub. #525, June, 1978, 209–218.

Smith S. W., Trahey G. E. and von Ramm O. T., "Phased array ultrasound imaging through planar tissue layers" , *Ultrasound in Medicine and Biology.* 12(3), 229–243, 1986.

Steinberg B. D., "Distortion correction by image feedback control" Valley Forge Research Center Quarterly Report #49, 54–58, 1986.

Steinberg B. D., and Subbaram H. M., "Self calibration of phased array using the Muller Buffington Theorem and transmitter location diversity" Valley Forge Research Center Quarterly Report #50, 31–45, 1986.

von Ramm O. T. and Smith S. W., "Beam steering with linear arrays," *IEEE Transactions on Biomedical Engineering,* BME-30 438–452, August 1983.

Wagner R. F., Smith S. W., Sandrik J. M., and Lopez H., "Statistics of Speckle in Ultrasound B-Scans," *IEEE Trans. Son. Ultrason.* 30(3) pp 156–163, May 1983.

Wells P. N. T., *Biomedical Ultrasonics,* Academic Press: London and New York, 1977.

The following patents disclose ultrasonic phased array systems having means for variable phasing of the array elements.

U.S. Pat. No. 4,566,459 to Umemura et al discloses a device and method for measuring the acoustic velocity inside a body for ultrasound imaging. The ultrasound diagnosis system determines whether the reflection signal of an object at a predetermined position is in-focus or out-of-focus and knows the actual acoustic velocity of the object from the assumed velocity when the reflection signal is in-focus.

U.S. Pat. No. 4,279,157 to Schomberg et al discloses a phased array scanning system which pre-calculates the transit time for acoustic beams, and is said to subsequently correct the variations of acoustic refractive indexed by comparing the calculated time against measured values.

U.S. Pat. No. 4,140,022 to Maslak and U.S. Pat. No. 4,149,420 to Hutchinson et al generally relate to ultrasound imaging.

SUMMARY OF THE INVENTION

The present invention relates to an on-line adaptive ultrasonic pulse echo phased array imaging device to correct for transducer phase aberrations and optimize spatial resolution. The invention uses the mean brightness of the ultrasound image texture of tissue parenchyma in a small region of interest as a quality factor. The mean brightness in the region is maximized by the image sharpening procedure as the sectored phased array scan data is varied on-line. The invention differs from the prior art ultrasound imaging which only used individual point sources as a phase synchronizing target. Such point sources are rarely present in the body. The invention differs from the image sharpening techniques of optical astronomy (spatially incoherent), by operating in a spatially coherent imaging system such as ultrasound or radar. A novel aspect of the new techniques is the tracking of mean image brightness over a region of primarily uniform image texture such as speckle, whereas the astronomical technique operated on only targets within the iso-planatic patch whether point targets (stars) or extended sources (planets) with bright spots. Such an indiscriminate adaptive processor does not perform adequately for spatially coherent imaging.

Nothing in the prior art, including the documents discussed above, discloses the on-line adaptive ultrasound pulse echo phased array system of the present invention.

It is therefore an object of the invention to overcome defects in the prior art, such as indicated above.

Another object of the invention is to provide for improved ultrasonic imaging.

It is yet another object of the present invention to provide an on-line adaptive ultrasonic pulse echo phased array imaging device which corrects for transducer phase aberrations and optimizes spatial resolution.

It is a further object of the present invention to provide a device which uses the mean brightness of the ultrasound image of tissue parenchyma in a small region of interest as a quality factor.

It is yet a further object of the present invention to provide a device in which the mean brightness in the region is maximized by the image sharpening procedure as the sectored phased array scan is varied on-line.

It is still a further object of the present invention to provide an adaptive phased array imaging system using spatially coherent radiation which employs an image sharpening process which maximizes the average brightness of image texture, that is, coherent speckle, within a selected region of interest by varying the phased array scan data of array elements for all image lines within the region.

Still other objects, features and attendant advantages of the present invention will become apparent to those skilled in the art from a reading of the following detailed description of the embodiments constructed in accordance therewith, taking into conjunction with the accompanying drawings.

BRIEF DESCRIPTION OF THE DRAWINGS

The invention of the present application will now be discussed in more detail with reference to the preferred embodiments of the device, given only by way of example, and with reference to the accompanying drawings, in which.

DETAILED DESCRIPTION OF THE PREFERRED EMBODIMENTS

Figure 1:
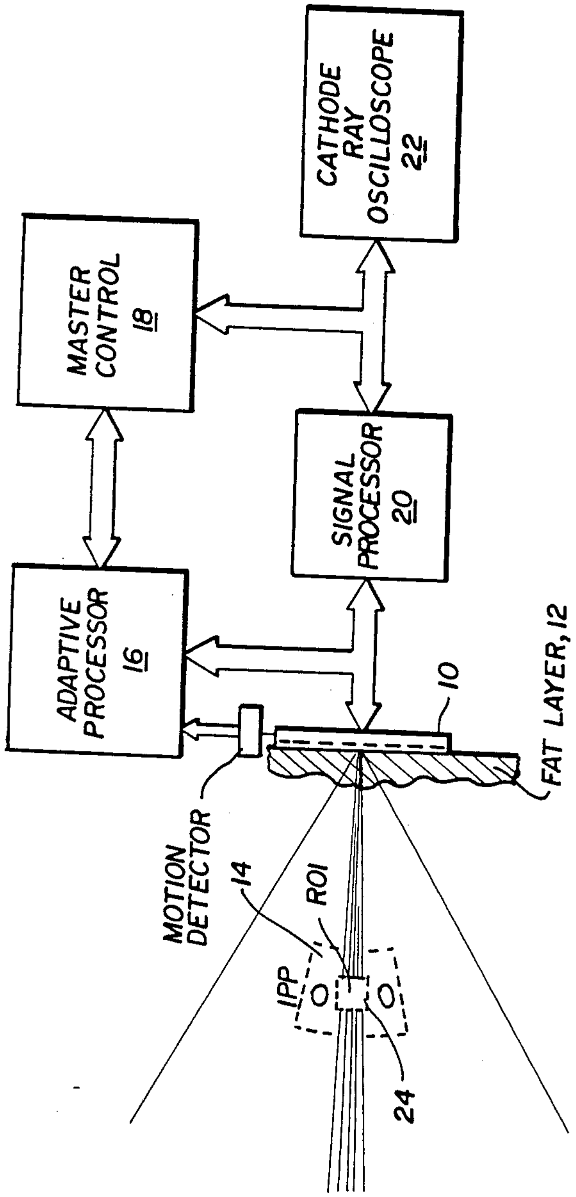
FIG. 1 is a block diagram showing a sector scan image of an abdominal organ parenchyma produced by the phased array imaging system according to the present invention.

FIG. 1 depicts a sector scan image of an abdominal organ parenchyma produced by an eight element sectored phased array imaging system 10. The image shows the fat and muscle layers 12 of inhomogeneous thickness at the apex of the scan. The presence of these layers across the eight element transducer array produces the undesired phase aberrations to be overcome. The phase aberrations are reasonably consistent over an iso-planatic patch superimposed on the image by the large dashed box marked IPP 14. Also superimposed within the IPP 14 is a small region of interest ROI 24. The overall image is characterized by a largely uniform texture consisting primarily of the ultrasound speckle interference pattern punctuated occasionally by discrete structures such as blood vessels.

The operation of the system proceeds as follows. The sectored phased array 10 can operate in conventional mode (see von Ramm et al, 1983) in which a no phase aberration condition is assumed, or in adaptive mode. During conventional operation of the sector scanner, the user positions the sector image so that the IPP window falls over structures of interest while the ROI contains no discrete structures, only uniform texture as shown in FIG. 1. At any time, however, the user can then initiate the adaptive mode by pushing a button, at which time the several independent image lines which fall within the ROI are obtained sequentially. The average image brightness is measured within the ROI and stored. Next, the phased array scan data for a single transducer element is changed for those same image lines in the ROI, a new ROI brightness is measured and compared to the original. The process is repeated in turn for each array element until the mean image texture brightness reaches a maximum. At that point, the diffraction limited resolution is optimized in the IPP by modifying the phased array scan data for all image lines in the IPP. The optimized phased array scan data is used until a motion detector attached to the transducer indicates that the transducer has moved significantly. At that time, the phased array system reverts back to the original phased array data of conventional mode and the image adaptive mode is ready again to be enabled.

The operation of a preferred embodiment of the system will now be described in more detail. Alternative implementations will also be discussed. The described construction is that of an adaptive sectored phased array, but the system can also be used for the more simple cases of an adaptive annular phased array or an adaptive linear sequential phased array with few modifications. The transducer array includes 8 piezoelectric elements in this example. The concepts of this description can be extended to any number of elements. The processor operation may be carried out for each individual array element, or in groups of elements to speed up the operation and enhance the before/after brightness difference.

FIG. 1 shows a block diagram of the imaging system which includes a Phased Array Transducer with Motion Detector 10, the master Control (MC) 18, the Signal Processor 20, the Adaptive Processor 16, and the Cathode Ray Oscilloscope 22. The function and operation of each of these components will be described for the example system. This example imaging system produces 128 image lines for an eight element array. Each image line contains six receive mode focal zones providing dynamic focusing in receive. In describing the system, it is helpful to consider its operation first in conventional phased array mode. In the conventional mode, the Master Control (MC) 18 regulates the function of the imaging system.

Figure 2A:
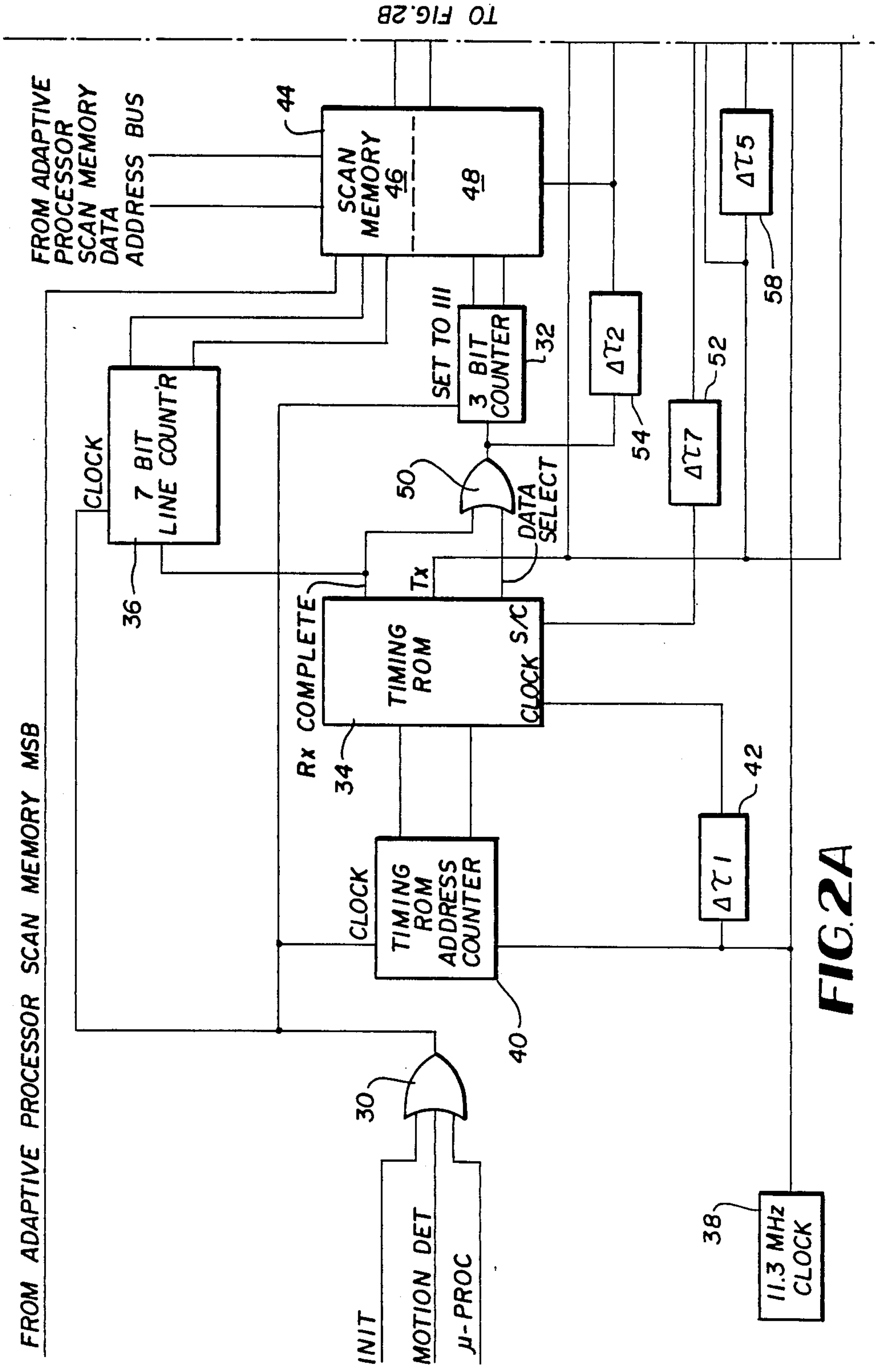
FIGS. 2A and 2B are schematic representations of the master control according to the present invention.
Figure 2B:
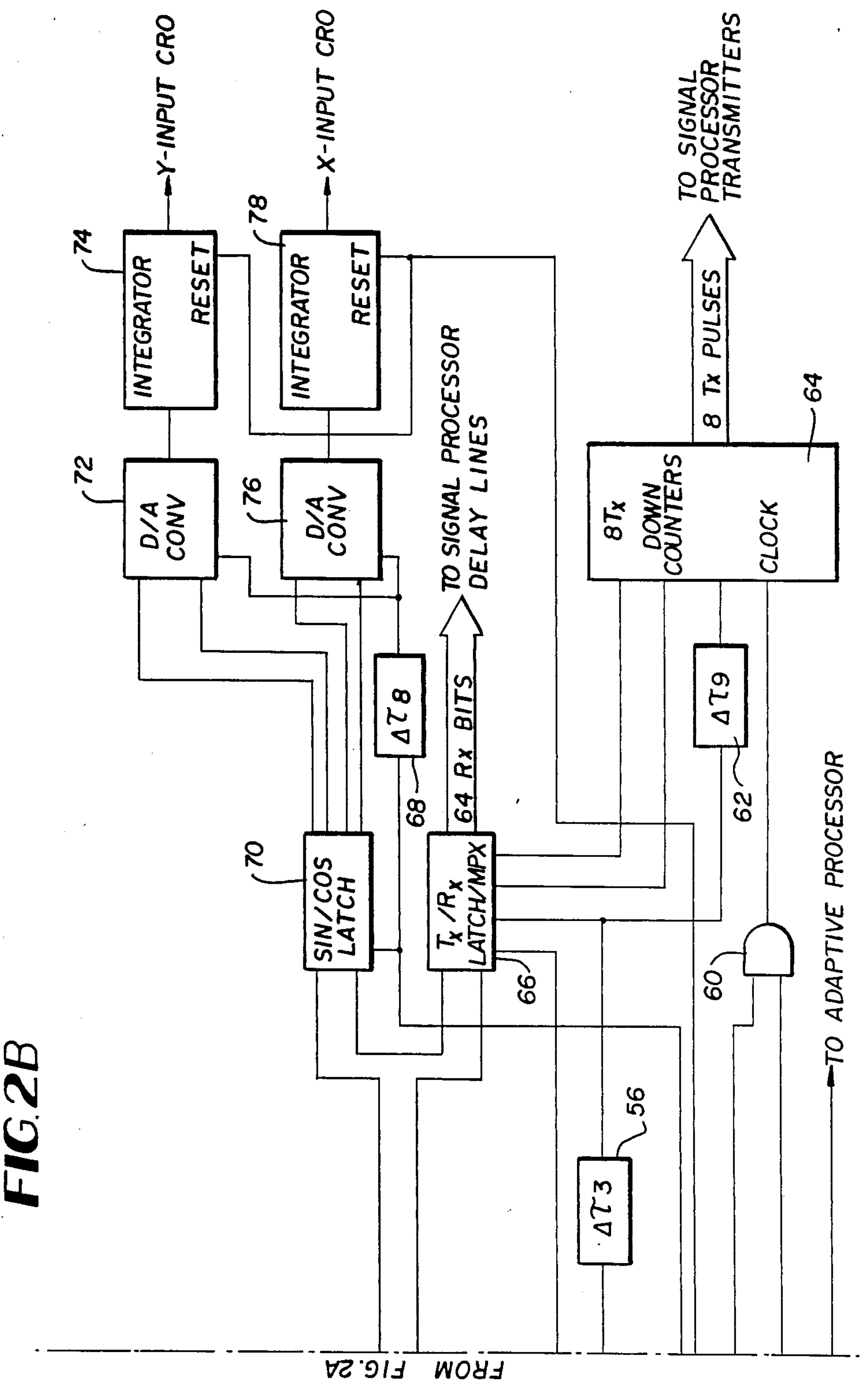

FIG. 2 is a schematic of the Master Control 18. In conventional mode, an external input signal (such as the closing of a switch), denoted by INIT, begins operation of the imaging system through OR gate 30 by initiating several functions of the master Control. The INIT signal initiates the three bit counter 32 by setting it to 111. INIT also clears the Timing ROM Address Counter 40 and the 7 bit line counter 36.

This implementation of the imaging system is paced by an 11.3 MHz master clock 38, resulting in a pulse rate of one pulse approximately ever 89 nsec. The clock pulses are sent to the Timing ROM Address Counter 40 which then increments the address of the Timing ROM 34 every 89 nsec. The Timing ROM 34 is also cycled by the master clock pulses after a preselected delay, 42 $\Delta\tau 1$. The Timing ROM 34 is a Read Only Memory, 4 bits wide and several thousands of bits long depending on the maximum range of echo information in the image and the number of image lines. The data contained in the Timing ROM 34 has been calculated off-line according to the conventional techniques of phased array imaging devices and is loaded into the Timing ROM 34 prior to the operation of the imaging system.

Figures 3, 4:
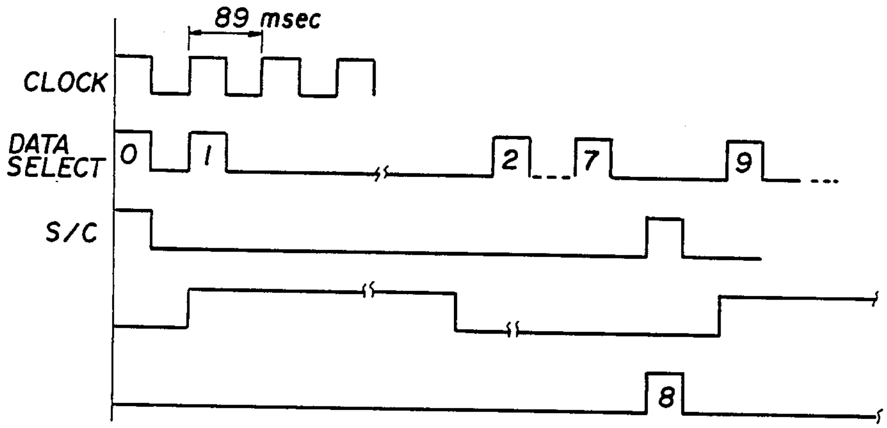
FIG. 3 is a timing diagram showing the operation of the system according to the present invention.
FIG. 4 illustrates a map of the scan memory according to the present invention.

The Timing ROM 34 data provide accurate timing pulses to signal the transmission and reception of the 128 ultrasonic image lines. The 4 bits of the Timing ROM 34 include the sine/cosine bit (S/C), the Data Select bit, the Transmit bit (Tx), and the Receive Complete bit (Rx complete). A diagram indicating the relative timing of these signals and the pulses of the master clock are shown in FIG. 3. In the Master Control 18, the Scan Memory 44 contains the phased array sector scan delay data for transmit and receive. In conventional operation, the lower portion of this memory is used (Scan Memory 46) and the data is calculated off-line assuming the geometry and uniform tissue velocity (1540 m/sec) of phased array beam steering (see von Ramm et al, 1983).

The most significant bit of the scan memory is set when the scanner operates in adaptive mode shifting to the upper Scan Memory 48. Initially the phase data in the two scan memory portions 46 and 48 are identical. The next seven most significant bits of the Scan Memory address are composed of the output of the seven bit image Line Counter 36 corresponding to 128 image lines. The three least significant bits of the Scan memory address consists of the output of the three bit counter 32 which was initialized by being set to 111 by the INIT signal. The three bit counter 32 is incremented by the output of OR gate 50 whose inputs are the Data Select bit and the Rx complete bit of the Timing ROM 34. Thus each address in the Scan memory 44 is uniquely determined by the 11 bit word resulting from the combination of the 1 bit Conventional/Adaptive mode choice, the 7 bit image Line Counter 36 output and the three bit Data Select counter 32.

FIG. 4 shows a map of the Scan Memory 44 which contains the data for the two independent Scan Data sets. Each data set includes the data for (1) the display steering angle, (2) 128 focused transmit steering angles, and (3) 128 receive steering angles at six focal zones. Each scan data set is divided into 128 blocks corresponding to each of the 128 image lines. Each block contains eight words each of 64 bits. In the first word of each block, the 8 MSB's contain the sine each image line of the sectored phased array steering angle of FIG. 1. The next 8 MSB's contain the cosine of the sectored phased array steering angle. The remaining bits of the first word of each block are not in use. In the second work of each block, the 64 bits contain the transmit timing data for the eight transducer elements of the phased array transducer. There are eight bits of control data for each of the eight transducer elements. The next six words of each block contain the receive mode data of six focal zones. As in the transmit word, there are eight bits of receive mode control data for each of the eight transducer elements. The two data sets of 128 blocks, each block containing eight words, result in a scan memory size of 2048 words, addresses 0 to 2047, each word of 64 bits. Scan data containing more than 128 image lines or more than 8 transducer elements would require larger memories.

As shown in FIGS. 2 and 3, after the INIT, the Data Select bit (0) is set which increments the three bit counter 32 to 000 and sets the Scan Memory 44 address at 00000000000, the address of the sine/cosine word of image line #1. The Scan Memory 44 is cycled by the Data Select bit through OR gate 50 after a suitable delay 54 Δτ2, and the Scan memory data is passed to the sin/cos latch 70. Simultaneously with the Data Select bit (0), the sine/cosine bit (s/c) is set. After a suitable delay 52, 7, the sin/cos Latch 70 is cycled and the 8 MSB's, the sine word, moves to the sine D/A convertor 72 while the next 8 MSB's, the cosine word, moves to the cosine D/A convertor 76. After further suitable delay 68 Δτ8, the D/A convertors are cycled and the sine and cosine data are sent as an analogue voltage levels to the input of the sine θ integrator 74 and cosine θ integrator 78.

On the following clock pulse, the Data Select bit (1) is set again as shown in FIG. 3. The Scan memory address now corresponds to that of the transmit data of the first image line, and this transmit data is passed to the Tx/Rx Latch/MPX 66 after delay 54 Δτ2. After a further short delay 56 Δτ3, the Tx/Rx Latch/MPX 66 is cycled and the data passes to its next destination depending on the direction of the Tx/Rx Latch/MPX 66. The direction of the Tx/Rx Latch/MPX 66 is determined by the Transmit bit of the Timing ROM 34 which is set to initiate the transmit acoustic burst simultaneously with Data Select (1). This bit is sent to the Tx/Rx Latch/MPX 66. If the bit is set, the direction of Tx/Rx Latch/MPX data flow is such that the data are sent to the 8 Transmit Down Counters 64. Eight bits of data per Down Counter are loaded at the time of the Data Select bit after delay 62 Δτ9.

Figure 5:
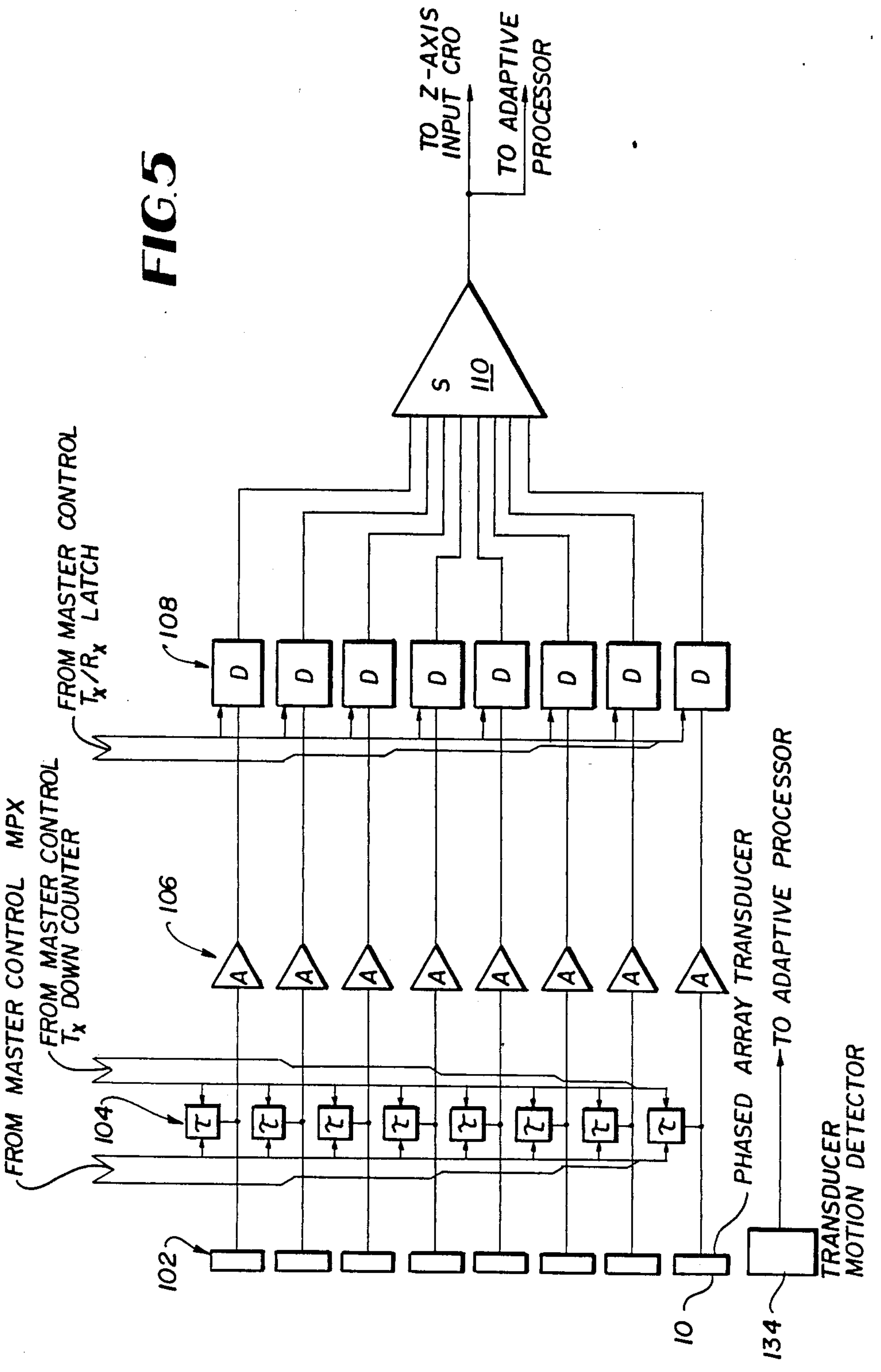
FIG. 5 is a schematic representation of the signal processor according to the present invention.

The Transmit of the Timing ROM 34 also forms one input to AND gate 60 suitably delayed by delay 58 Δτ5 so as to occur after delay 62 Δτ9. The master clock pulses form the second input to AND gate 60 whose output serves as the clock for the down counters 64 so that they now begin to count down at 11.3 MHz. As each counter reaches zero, it sends the properly timed transmit trigger pulse to its respective transmitter circuit (T) shown in the Signal Processor 20 (FIG. 5). The transmit bit also resets the sine/cosine integrators 74 and 78 so that they initiate their operation at the time of the ultrasonic transmit burst. The outputs of the integrators pass to the X and Y inputs of the Cathode Ray Oscilloscope 22 and provide the deflection voltages for the display of the sector scan format.

As shown in FIG. 3, at the completion of the transmit process, the Tx bit goes low, the Data Select bit is set again so that the Scan Memory address is incremented to 2. The Scan Memory receive data for the first focal zone now passes through the Tx/Rx Latch/MPX 66, which has been switched to permit data flow to the Signal Processor 20. Thus, the 64 bits of the receive data now pass to the control inputs of delay lines (D) of the Signal Processor 20. After a predetermined time, all the echo data from the first focal zone has been received by the imaging system, the Data Select bit is again set and the 64 bit delay line control data for the second receive mode focal zone passes to the Signal Processor 20. As shown in FIG. 3, this process continues for 6 focal zones, Data Select (2)-(7). When all the echo data from distances out to the predetermined maximum range has been received by the imaging system, the Receive Complete bit is set in the Timing ROM 34. The Rx Complete bit increments the 7 bit image line counter 36 and the three bit counter 32 through OR gate 50. The output of the 3 bit counter 32 is now 000. The address of the Scan memory 44 is now 8, the first word of the scan memory 46 second block. Simultaneously the second sine/cosine bit is set. Shortly thereafter, the Tx bit is set for the second time and the acoustic burst is transmitted for the second image line of echo data acquisition.

These operations are continued until the 128 image lines of the frame are obtained. At that time, the address of the Timing ROM Address Counter 40 overflows to repeat the following image frame.

SIGNAL PROCESSOR

FIG. 5 is a schematic of the Signal Processor 20. The figure shows the eight transducer elements 102 of the phased array 10 and the eight associated transmitters (T) 104. During the imaging process, the correct transmit timing pulses are sent in parallel to the transmitter 104 from the transmit down counters 64 of the MC 18. The image line echoes return in parallel through the amplifiers (A) 106 to delay the lines (D) 108. The amplifiers 106 include the normal capabilities of time gain compensation and/or non-linear amplification (logarithmic compression). The lengths of the delay lines 108 are determined by the receive mode scan memory data of MC 18. The delay lines 108 may be analog or digital. The output of the delay lines 108 form the multiple inputs of the summing amplifier 110, (S). This amplifier 110 includes the normal operations of video processing in a phased array imaging system including detection, filtering and video amplification. The output of the amplifier 110 (S) is sent to the Z-axis input of the Cathode Ray Oscilloscope 22 for display. Alternatively the display operation can be accompanied by analog or digital scan conversion.

ADAPTIVE MODE OPERATION

The phased array imaging system initiates adaptive mode operation at the push of a button on the transducer by the operator when he has positioned the ROI window 24 over a patch of tissue parenchyma texture. After the operator has initiated the adaptive mode, by pushing the button, the transducer motion detector operates to initiate adaptive processing each time the operator has moved the transducer greater than a predetermined distance (described more fully below).

Figure 6:
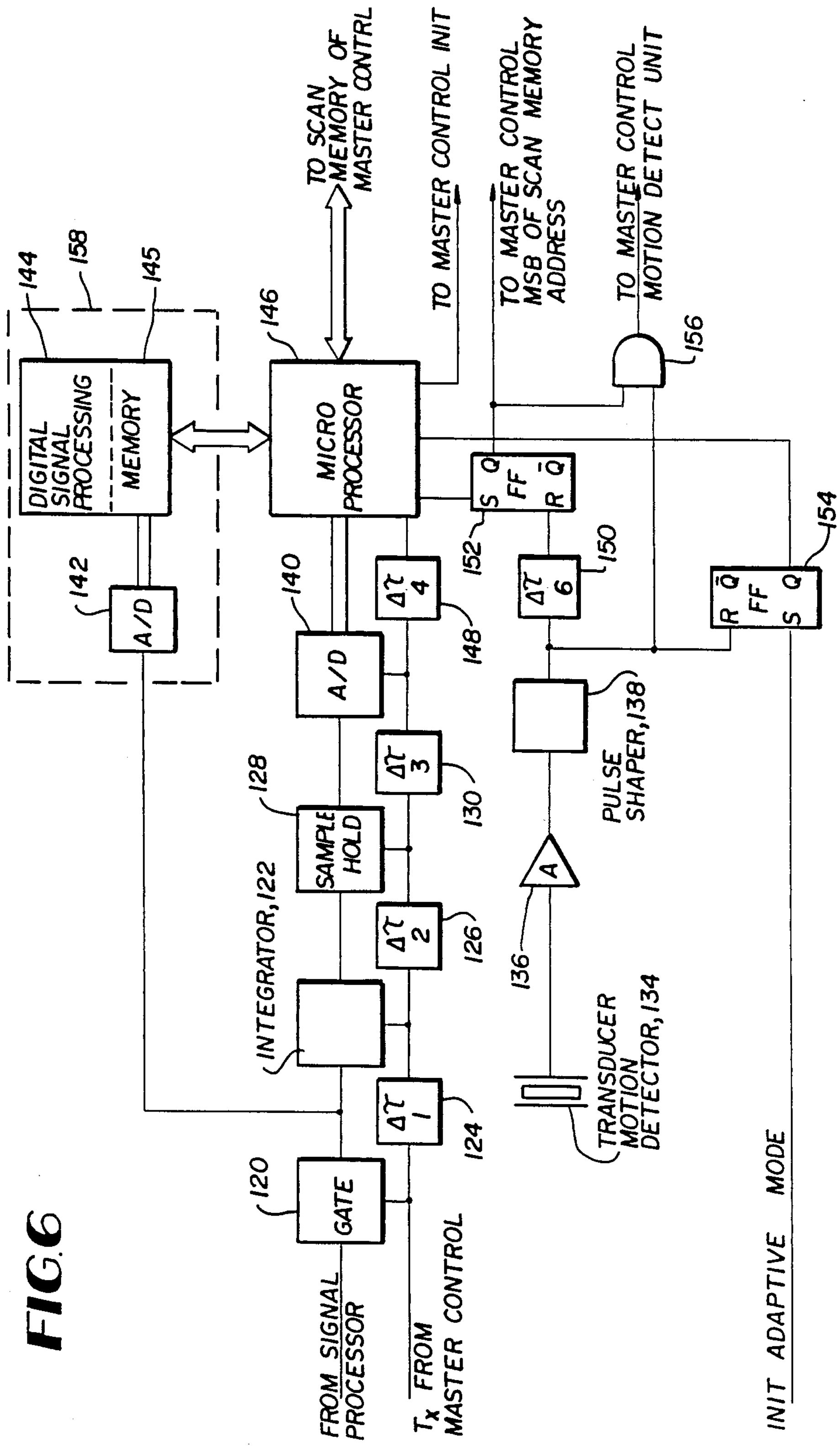
FIG. 6 is a schematic representation of the adaptive processor according to the present invention.

When adaptive processing is initiated the Adaptive INIT begins the operation of the microprocessor in the Adaptive Processor 16 by setting flip-flop 154, FF2 as shown in FIG. 6. The microprocessor 146 in turn suspends operation of the conventional phased array scanning by reinitializing the Master Control 18 through OR gate 30 after a short delay for initializing the microprocessor 146. At this time, operation of the adaptive mode begins as described below with reference to the Flow Chart in FIG. 7.

The Adaptive Processor uses the normal sequence of the Timing ROM 34 and Scan Memory 46 up to a point. Thus, the first image line of Scan Memory 46 up to a point. Thus, the first image line of Scan Memory 46 is obtained. However, it should be noted that line 1 stored in the Scan Memory 46 has been assigned to the first line of the image which crosses the ROI 24 in the sector scan of FIG. 1. The flexibility of a phased array system enables the image lines to be obtained in any order. The echo signal output of the summer/detector 110 S of the Signal Processor 20 passes to the Adaptive Processor 16 in parallel to its path to the CRO 22. In the Adaptive Processor 16 the echo signal from image line #1 passes through the adjustable range gate 120 which is triggered by the Tx pulse from the Timing ROM 34 of MC 18. The gate is set so that it contains only the target range within the ROI 24.

The output of the gate 120 then is integrated by integrator 122 after delay 124 $\Delta\tau 2$ and the integral value over the gate 120 is stored in the sample/hold 128 after delay 126 $\Delta\tau 2$ and digitized in the A/D convertor 140 after delay 130 $\Delta\tau 3$ and then stored after delay 148 $\Delta\tau 4$ in an accumulator (not shown) of the microprocessor 146. The complete operation takes place during the normal round-trip transit time of the ultrasound echo using the conventional timing of the ROM 34 of MC 18. The operation is then repeated for each independent image line (spaced one lateral resolution cell apart) in the ROI 24. In this example, five lines are obtained in the ROI 24 as shown in FIG. 1 requiring approximately 1 msec, assuming a maximum image range of 15 cm. Thus, an average image brightness of the five image lines within the ROI 24 is accumulated and stored in register B1 (not shown) of the microprocessor 146.

When the final line of the ROI 24 is obtained, the microprocessor 146 sets the Init bit again, reinitializing the Master Control 18. The bit is held while the microprocessor implements the memory update of the ROI image lines. The Tx/Rx 64 bit data words of each of the five ROI image lines for the focal zones within the range gate 120 are sent to the microprocessor 146 from Scan memory 46 of the MC 18. For element #1 of each word a new delay D=1 bit is added to the total delay. The one bit delay size is determined by the minimum delay of the Signal Processor Delay lines 108. A typical value of D is one-eighth wave-length of the ultrasound transducer.

The new phase delay words are then moved back to the MC 18 but to their equivalent addresses in Scan memory 48. If one assumes a transmit word and 3 receive mode focal zone words for the 5 ROI image lines, the total memory transfer and update time for array element #1 would require approximately 80 $\mu$ sec for a 1 MHz cycle time microprocessor. When the 1 bit, 1 element memory update is completed, the microprocessor 146 sets the flip-flop FF1 152 of the Adaptive Processor 16 whose Q output sets the most significant bit of the MC Scan Memory 44 so that the scanner uses Scan Memory 48 for the subsequent image lines. The microprocessor 146 also releases the adaptive Init bit so the Timing ROM 34 proceeds again to acquire the 5 ROI image lines using the modified data of scan memory 48. The new average image brightness is stored in register B2 (not shown) and compared to the original value in B1. If the new brightness in B2 exceeds the original image brightness, the adaptive processor 16 is moving in the right direction. The Tx/Rx phase delays for element #1 continue to be increased by 1 bit increments ($D=D+X$, $X=1$) until the new brightness is less than the previous value, i.e., B2<B1. This indicates that the proper phase delay for element #1 to maximize ROI image brightness has been found. This optimum delay increment D is then added to Scan Memory Data #1 for element #1 for all the image lines in the IPP 14 by moving them to the microprocessor 146 and returning them to Scan Memory 48.

If the Scan Data update for delay increase is immediately moving in the wrong direction (B2<B1, D=1, X=1). the direction of the data modification of element #1 is switched to delay decrease ($D=-1$, $X=-1$). The delay update and brightness measurement is now repeated until the maximum brightness is found and the phase delay data is modified for the IPP 14 for element #1. If one assumes a worst case for element #1 of moving one step, D in the wrong direction followed by four necessary steps in the right direction, $D=-4$, that process will require six Tx/Rx cycles of 5 ROI lines, requiring 5 msec total, plus the memory update of 100 ROI and IPP image lines which requires a total of 8 msec.

The total adaptive processor time for element #1 is 13 msec. A worst case total time for the adaptive processor 16 to optimize the phase delays of all eight elements throughout the IPP 14 is approximately 100 msec. When the optimization is complete, the Master Control 18 is initialized one last time and the scanner operates in conventional mode again albeit using the now optimized phase delay data of Scan Memory 48.

Figure 7A:
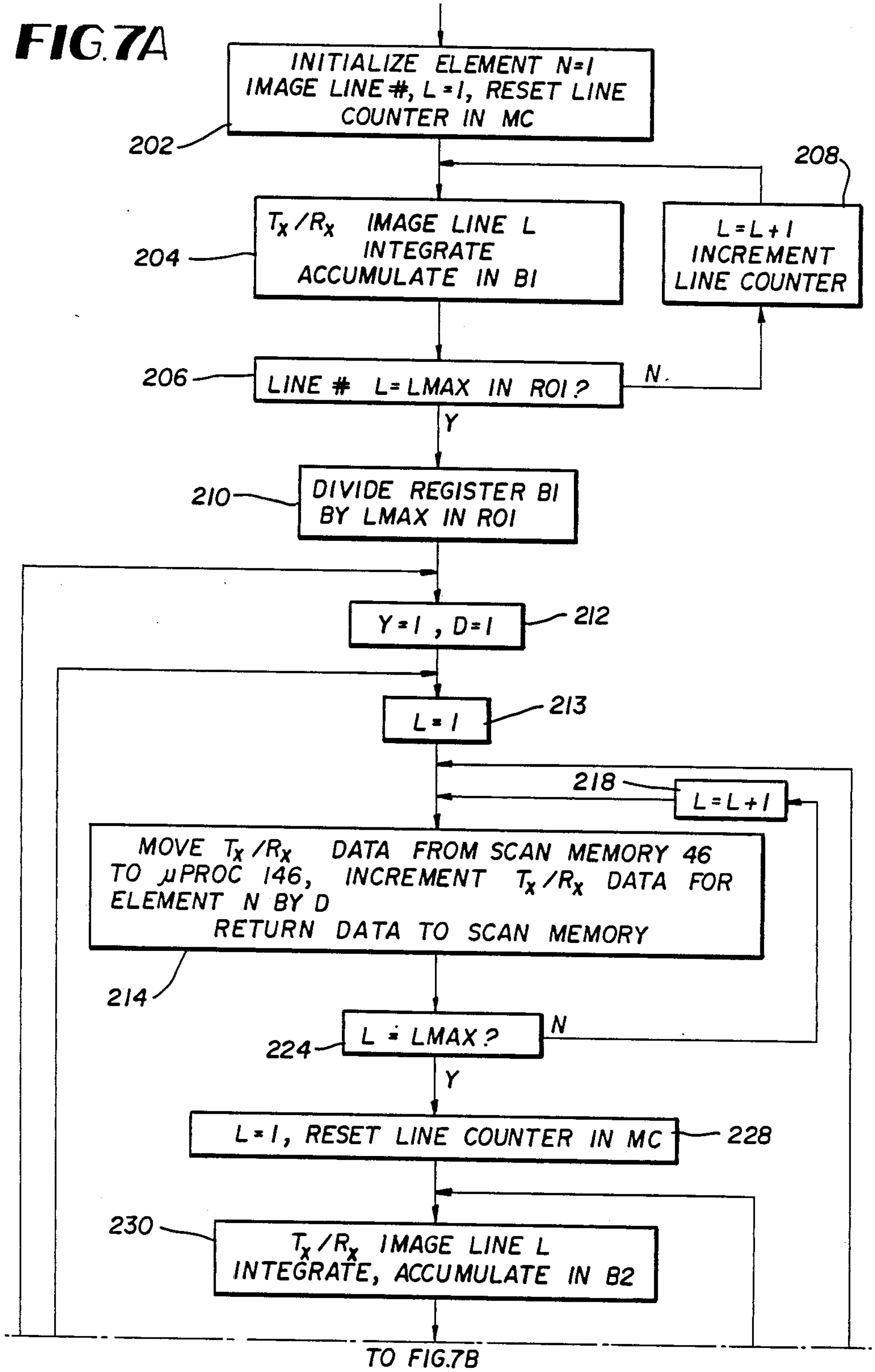
FIGS. 7A and 7B are flow charts of the adaptive processor operating in the adaptive mode according to the present invention.
Figure 7B:
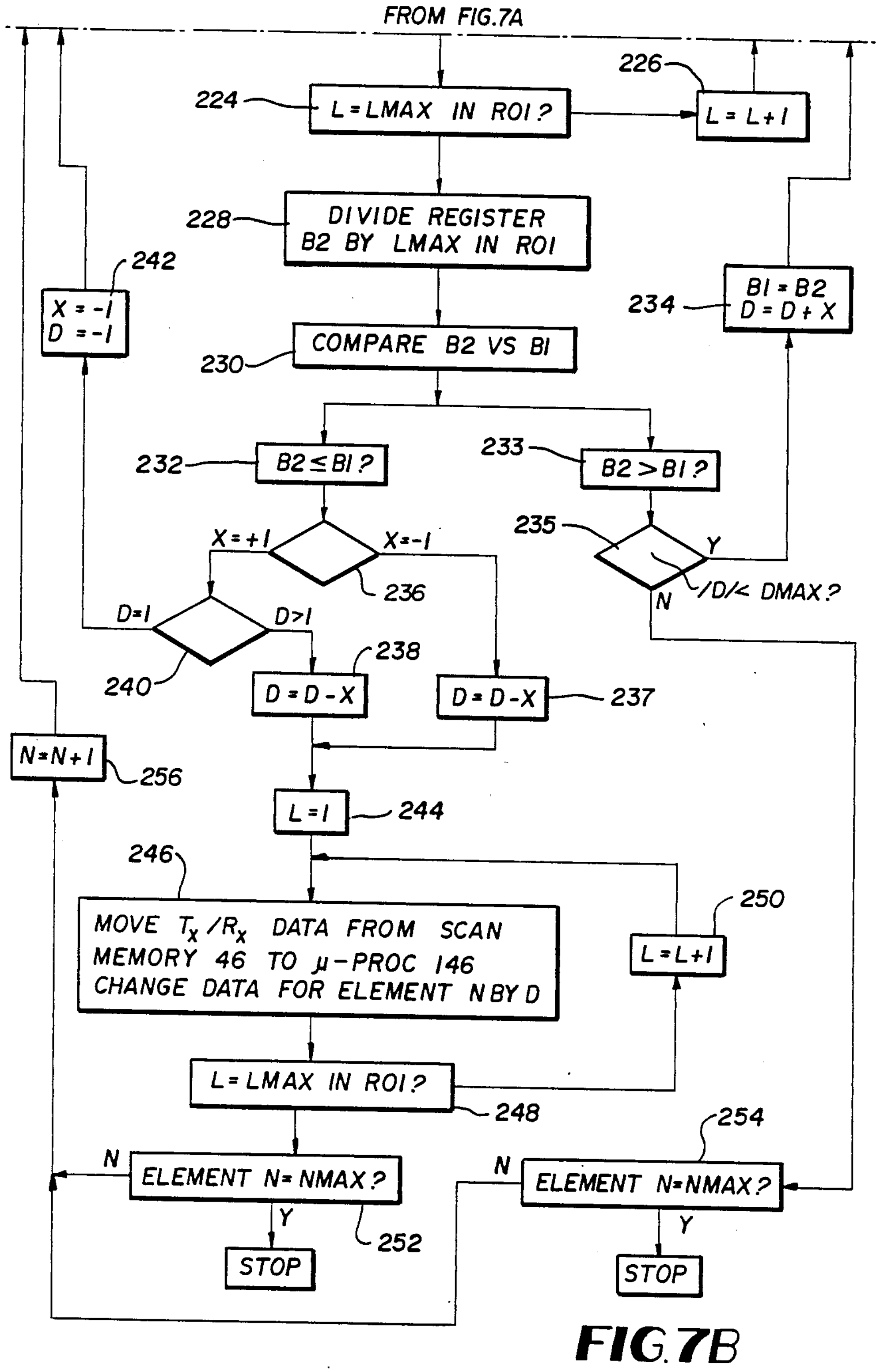

The Flow Chart shown in FIG. 7 will now be described. In general terms, in order to determine the optimum delay value that yields the brightest average image, the delay associated with each element in turn, is changed in increments of +1 or −1. For example, a delay increment of +1 is used at first. The average brightness for the ROI is determined and the total delay is incremented by +1 for element #1. If the image is brighter, the delay is being incremented in the correct direction. The delay is then incremented until the picture becomes dimmer. At that point, the maximum average image brightness has been reached, and the previous total delay value is used as the scan data for that element. If the second average image brightness is dimmer than the first, the delay is moving in the wrong direction. The delay increment is changed to −1 and is continually incremented by −1 until the maximum average image brightness is determined.

Referring now to the flowchart, when the adaptive processing mode is started, the element number N is initialized to 1, the image line number L is initialized to 1 and the line counter in the Master Control is reset at step 202. At step 204, after the transmit/receive operation in image line L the returning echo signal is integrated and accumulated in register B1. At step 206, it is determined whether the line number L is the maximum in the ROI. If so, at step 208 the line counter is incremented and control returns to step 204. If the last line in the ROI has been reached, the register B1 is divided by the number of lines in the ROI, LMAX, at step 210.

At step 212, X and D are set to 1. At step 213, L is set to 1, and at step 214 the Tx/Rx data from Scan Memory 46 are moved to the microprocessor. Tx/Rx data are incremented for element N by D and the data is returned to Scan memory 48. At step 216 it is determined whether the last line in the ROI has been reached. If not the line counter is incremented at step 218 and control is returned to step 214.

After the last line in the ROI has been reached (step 216), the line counter L is reset to 1 (step 220). At step 222, Tx/Rx and the image line L is integrated and accumulated in register B2. At step 224, it is determined whether the last line in the ROI has been reached. If not, the line counter is incremented (step 226) and control is returned to step 222.

After all lines have been processed, the value in register B2 is divided by the number of lines in the ROI, LMAX at step 228. At step 230, B2 is compared with B1.

At step 233, if B2 is greater than B1 and the absolute value of D is less than DMAX (usually λ)(step 235), the adaptive processor is still moving in the correct direction and the average image brightness is still increasing. Lambda (λ) refers to the wavelength of the signal; if the delay is greater than λ processing is stopped since a position on the sine wave has been reached which was previously examined.

At step 234, B1 is set to B2 and D is incremented by X. Control then returns to step 214 to remeasure the image brightness using the incremented D value.

At step 231, B2 is found be less than or equal to B1, indicating that the average image brightness has not increased. If X equals −1 (step 236) D is set to D+1 (step 237) and control passes to step 244. If X equals +1 (step 236) and D=+1 (step 240), D and X are both set to −1 (step 242) and control passes to step 214. Otherwise, D>1 so D is set to D-1 (step 238) and control passes to step 244, where L is set to 1. At step 246, the Tx/Rx data from Scan memory 46 is moved to the microprocessor and the data for element N is changed by D. At step 248 it is determined whether L is equal to the maximum lines in the ROI. If not, L is incremented at step 250. If so, and if at step 252, N is equal to the maximum number of elements, then processing stops. Otherwise at step 256, N is incremented and control returns to step 121.

The operation of the transducer motion detector 134 remains to be described. When the system is operating in the adaptive mode (either during memory update or during post-correction imaging) if the transducer is moved by the operator or if a large respiration occurs, the phase aberrations across the transducer will probably change so that the corrected phase data of scan memory 48 will no longer improve the image lateral resolution. For this reason, a transducer motion detector 134 is designed into the transducer head in the form of a piezoelectric accelerometer which generates a voltage signal transient from any motion. The motion detection signal passes to the amplifier A 136 in FIG. 6 and then passes through the pulse shaper 138 to produce a TTL pulse. The amplifier is adjusted with a threshold control to reject small motion signals which do not change the transducer phase aberrations. The output of the pulse sharper resets FF2 154 in FIG. 6 which halts the operation of the microprocessor 146. The pulse shaper output also resets FF1 152 after delay 150 Δτ5 in FIG. 6 so that the Q output goes low returning the MSB of the MC scan memory 44 to 0, thus returning the MC 18 to use scan memory 46. Finally, the output of the pulse shaper 138 is ANDed by AND gate 156 with the MSB of the scan memory 44 thus reinitializing the MC 18 only when the system has been operating in the adaptive mode. In this way, during adaptive mode operation, the adaptive processing will be automatically initiated each time the operator moves the transducer a distance large enough to render the previous phase data ineffective to correct for the phase abberations.

Of course, the Adaptive Processor can operate with more complexity. Tolerance limits can be placed on the brightness comparison of B2 or B1 to account for noise and drift in the brightness measures. Arrays of greater than eight elements require more time to correct. Phase delays of groups of elements can be corrected together to shorten processing time and to correct transducer aberration function of long correlation lengths. Phase increment (X) of larger size can be used to speed up the process. The starting point for the correction of element N+1 could be set depending on the best correction for element N. A check routine can be added to monitor phase corrections of greater then one wavelength. Instead of the average brightness in the ROI, a simple integral of the brightness can be used. Microprocessors are now available operating at 10 MHz (100 nsec cycle times) to shorten the memory updates significantly. Parallel receive mode processing, which has been developed for ultrasound scanning acquires many image lines (up to 8) for a single transmitted ultrasound pulse (See Shattuck, et al, 1984). This would significantly reduce pulse-echo times of flight at some compromise to signal to noise ratio.

The size of the ROI and number of image measurement line affects the signal to noise ratio of the brightness measurement. The severity of the transducer phase aberration determines the necessary size of the ROI and the available size of the IPP. For Adaptive Processors operating at maximum speed, the adaptive operation could be carried out on each image frame for several IPP's to correct the phase aberrations of the entire sector image in real time. If specular targets such as blood vessels intrude into the ROI, a matched filter can be passed over the ROI to eliminate these targets while leaving the speckle texture undisturbed. Other image sharpening quality factors could be used instead of image brightness. These include the image intensity raised to any power.

Although the ROI in FIG. 1 is shown to consist of five lines, as few as one line can be used where a longer length is used to assure adequate signal to noise ratio.

There is a final alternate implementation of the Adaptive Processor as shown by the Digital Signal Processing Chip 158 in the dashed box in FIG. 6. In this implementation the B-mode image signal for each ROI line passes from the range gate through the A/D converter 142 to be stored in memory 145. The digital signal processing chip 158 calculates on-line the ACVF or its Fourier transform, the noise power spectrum in the lateral direction via a Fast Fourier Transform (FFT) calculation. The full width half maximum of the speckle texture size is then calculated within the ROI 24. As in the flow chart for ROI image brightness, the ACVF is compared before and after phase data modification to maximize ACVF main lobe full width half maximum to optimize the sector scan phase data within the IPP 14. Digital signal processing chips are now available, such as the Texas Instruments 32010 to accomplish the Fourier Transform operation at high speeds enabling the ACVF Adaptive Processor to operate at equivalent rates to the brightness test Adaptive Processor.

It is also possible to construct the system according to the present invention which employs an image sharpening process which maximizes the average size of image texture (coherent speckle) within a selected region of interest by varying the phased array scan data of the array elements for the image lines within the region.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning in range of equivalents of the disclosed embodiments. It is to be understood that the phraseology or terminology employed herein is for the purpose of description and not of limitation.

What is claimed is:

1. A method of ultrasonic imaging comprising the steps of:

placing a transducer, having at least one transducer element, over a region of interest;

entering an adaptive mode of operation which comprises performing the following steps for each element of the transducer:

(a) measuring average brightness in the region of interest for normal operation;

(b) incrementing phased array scan data for said element and for the region of interest;

(c) obtaining a value representing the average image brightness of the region of interest responsive to the phased array scan data;

(d) repeating steps (a) through (d) until a maximum average image brightness has been reached;

updating the phased array scan data for the region of interest using the phased array scan data which produced the maximum average image brightness; and entering the normal mode of operation using the updated phased array scan data.

2. The method according to claim 1, wherein said region of interest comprises at least one image line, and said obtaining a value comprises the steps of:

obtaining a line value representing the average image brightness for each image line; and dividing the line value by the number of lines in the region of interest.

3. The method according to claim 2, wherein the phased array scan data comprises transmit/receive phase delay data.

4. The method according to claim 3, further comprising the steps of:

determining when the transducer has been moved beyond a predetermined distance; and automatically reentering the adaptive mode of operation responsive to the distance determination.

5. The method according to claim 3, wherein said transit/receive phase delay data is incremented by one delay unit.

6. The method according to claim 5, wherein said adaptive mode further comprises the step of determining when a maximum average image brightness has been reached for each element, said step of determining comprising the steps of:

comparing a recently obtained average image brightness value to a previous average image brightness value obtained in the immediately previous iteration of steps (a) through (c);

if the recently obtained average image brightness value is less than the previous image brightness value, decreasing the phase delay data by one delay unit indicating maximum average image brightness has been reached; and if the recently obtained average image brightness value is greater than the previous image brightness value, increasing the phase delay data by one delay unit indicating maximum average image brightness has not been reached.

7. An ultrasonic phased array imaging system having a normal mode and an adaptive mode of operation, said system comprising:

a transducer, having at least one element, for recording an image of a region of interest;

adaptive means for adjusting phased array scan data associated with each element of the transducer, said adaptive means comprising:

(a) means for incrementing the phased array scan data for the element and for the region of interest;

(b) averaging means for obtaining a value representing the average image brightness of the region of interest responsive to the phased array scan data;

(c) determining means for determining when a maximum average image brightness has been achieved;

means for updating the phased array scan data for the region of interest using the phased array scan data which produced the maximum average image brightness; and means for entering the normal mode of operation.

8. The apparatus according to claim 7, wherein said region of interest comprises at least one image line and said averaging means comprises:

imaging means for obtaining a line value representing the average image brightness for each image line; and dividing means for dividing the line value by the number of lines in the region of interest.

9. The apparatus according to claim 8, wherein the phased array scan data comprises transmit/receive phase delay data.

10. The apparatus according to claim 9, further comprising:

motion detection means for determining when the transducer has been moved beyond a predetermined distance; and means responsive to the distance determination for automatically reentering the adaptive mode of operation.

11. The apparatus according to claim 9, wherein said means for incrementing said transmit/receive phase delay data increments said data by one delay unit.

12. The apparatus according to claim 11, wherein said adaptive means further comprises determining means for determining when a maximum average image brightness has been reached for each element, said determining means comprising:

comparing means for comparing a recently obtained average image brightness value to a previous average image brightness value obtained in the immediately previous iteration of steps (a) through (c);

subtracting means for decreasing the phase delay data by one delay unit responsive to the recently obtained average image brightness value being less than the previous image brightness value; and adding means for increasing the phase delay data by one delay unit responsive to the recently obtained average image brightness value being greater than the previous image brightness value.

13. An ultrasonic phased array imaging system, said system having an adaptive mode and a normal mode comprising:

a transducer having a plurality of elements for generating signals representing an image;

an adaptive processor for adapting phased array scan data for each element to provide maximum average brightness for an image of a region of interest;

a master control for regulating the imaging system when operating in the normal mode;

a signal processor for processing the signals received from said transducer; and display means for displaying said processed signals.

14. The system according to claim 13, wherein said master control comprises:

a timing memory for storing timing pulses for signally transmission and reception of image lines;

a timing address counter connected to said timing memory for addressing said timing memory;

a scan memory for storing phased array scan delay data;

first and second counters for accessing said scan memory; and integrator means connected to outputs of said scan memory for providing deflection voltages for providing X-axis and Y-axis inputs to said display means.

15. The system according to claim 13, wherein said signal processor comprises:

a plurality of transmitters associated with said plurality of elements;

a plurality of amplifiers having inputs connected to said plurality of elements and outputs;

a plurality of delay lines having inputs connected to the outputs of said plurality of amplifiers and outputs;

a summing amplifier having inputs connected to said outputs of said plurality of delay lines and an output for providing Z-axis input to said display means.

16. The system according to claim 13, wherein said adaptive processor comprises:

a first flip-flop for initiating adaptive processor operations;

means for incrementing the phased array scan data for each element and for the region of interest;

averaging means for obtaining a value representing the average image brightness of the region of interest responsive to the phased array scan data;

determining means for determining when a maximum average image brightness has been achieved; and means for updating the phased array scan data for the region of interest using the phased array scan data which produced the maximum average image brightness.

17. A method of operation the ultrasonic phased array imaging system according to claim 13, said method comprising the steps of:

placing a transducer, having at least one element, over a region of interest;

entering the adaptive mode of operation which comprises performing the following steps for each element of the transducer;

(a) incrementing phased array scan data for the element and for the region of interest;

(b) obtaining a value representing the average image brightness of the region of interest responsive to the phased array scan data;

(c) repeating steps a) through c) until a maximum average image brightness has been reached;

updating the phased array scan data for the region of interest using the phased array scan data which produced the maximum average image brightness; and entering the normal mode of operation.

18. The method according to claim 17, wherein said region of interest comprises at least one image line and said step of obtaining a value comprises the steps of:

obtaining a line value representing the average image brightness for each image line; and dividing the line value by the number of lines in the region of interest.

19. The method according to claim 18, further comprising the steps of:

determining when the transducer has been moved beyond a predetermined distance; and automatically reentering the adaptive mode of operation responsive to the distance determination.

20. The method according to claim 19, wherein said adaptive mode further comprises the step of determining when a maximum average image brightness has been reached for each element, said step of determining comprising the steps of:

comparing a recently obtained average image brightness value to a previous average image brightness value obtained in the immediately previous iteration of steps (a) through (c);

if the recently obtained average image brightness value is less than the previous image brightness value, the phase delay data is decreased by one delay unit indicating maximum average image brightness has been reached; and if the recently obtained average image brightness value is greater than the previous image brightness value, the phase delay data is increased by one delay unit indicating maximum average image brightness has not been reached.

* * * * *